United States Patent
Boese et al.

(10) Patent No.: US 7,734,329 B2
(45) Date of Patent: Jun. 8, 2010

(54) METHOD FOR PRE-INTERVENTIONAL PLANNING OF A 2D FLUOROSCOPY PROJECTION

(75) Inventors: Jan Boese, Eckental (DE); Thomas Redel, Poxdorf (DE)

(73) Assignee: Siemens Aktiengesellschaft, Munich (DE)

( * ) Notice: Subject to any disclaimer, the term of this patent is extended or adjusted under 35 U.S.C. 154(b) by 415 days.

(21) Appl. No.: 11/484,196

(22) Filed: Jul. 11, 2006

(65) Prior Publication Data

US 2007/0021668 A1    Jan. 25, 2007

(30) Foreign Application Priority Data

Jul. 12, 2005    (DE) ................ 10 2005 032 523

(51) Int. Cl.
*A61B 5/05* (2006.01)
(52) U.S. Cl. .................................... 600/427
(58) Field of Classification Search ........ 600/407, 600/408, 425–429; 345/418–428; 382/154, 382/285
See application file for complete search history.

(56) References Cited

U.S. PATENT DOCUMENTS

| | | | |
|---|---|---|---|
| 6,198,794 B1 * | 3/2001 | Peshkin et al. | ........ 378/42 |
| 6,470,207 B1 * | 10/2002 | Simon et al. | ........ 600/426 |
| 6,711,432 B1 * | 3/2004 | Krause et al. | ........ 600/427 |
| 2001/0036245 A1 * | 11/2001 | Kienzle et al. | ........ 378/4 |
| 2002/0045817 A1 | 4/2002 | Ichihashi | |
| 2003/0220555 A1 * | 11/2003 | Heigl et al. | ........ 600/407 |
| 2004/0009459 A1 * | 1/2004 | Anderson et al. | ........ 434/262 |
| 2005/0049486 A1 * | 3/2005 | Urquhart et al. | ........ 600/429 |
| 2005/0089143 A1 | 4/2005 | Nakano et al. | |
| 2007/0115204 A1 * | 5/2007 | Budz et al. | ........ 345/6 |

FOREIGN PATENT DOCUMENTS

| | | |
|---|---|---|
| DE | 103 23 008 A1 | 12/2004 |
| EP | 1 504 713 A1 | 2/2005 |
| EP | 1 510 182 A2 | 3/2005 |
| WO | WO 01/87136 A2 | 11/2001 |

* cited by examiner

*Primary Examiner*—Long V Le
*Assistant Examiner*—Saurel J Selkin

(57) ABSTRACT

Method for pre-interventional planning of a 2D fluoroscopy projection for an interventional entry using a fixed instrument, comprising the following steps:
a) Recording a 3D data set,
b) Planning the intervention,
c) Planning the optimum projection direction,
d) Registering the 3D data set with a navigation system and a 2D fluoroscopy system,
e) Transmission of the intervention data to the navigation system,
f) Computing the position of the fluoroscopy system, and
g) Executing the interventional entry under fluoroscopy.

13 Claims, 3 Drawing Sheets

METHOD FOR PRE-INTERVENTIONAL PLANNING OF A 2D FLUOROSCOPY PROJECTION

CROSS REFERENCE TO RELATED APPLICATIONS

This application claims priority of German application No. 10 2005 032 523.8 filed Jul. 12, 2005, which is incorporated by reference herein in its entirety.

FIELD OF THE INVENTION

The invention relates to a method for pre-interventional planning of a 2D fluoroscopy projection for an interventional entry using a fixed instrument.

BACKGROUND OF THE INVENTION

The process of planning interventions with a fixed instrument, for example an aspiration needle, based on pre-interventionally recorded data sets, is already known. These data sets can be obtained by 3D angiography, CT or MR investigation. The planning undertaken in advance can then be transferred to a navigation system or a system for orientation of the fixed instrument or the aspiration needle. Such a system is for example a stereotactic frame, which allows pinpoint alignment and positioning of the aspiration needle. The case can arise however in which the aspiration needle or another fixed instrument has to pass within a very short distance of critical structures such as vertebrae, organs or blood vessels. In order not to endanger the patient a continuous monitoring of the position of the needle is necessary. The direction of projection must be defined within the context of pre-interventional planning. The direction of projection, which can be imagined as a straight line through the tube focus and the center of the detector of the fluoroscopy system, is set by corresponding positioning of the C-arm of the fluoroscopy device. This setting is made manually, based on the experience of the operator, with a number of steps sometimes being required. The disadvantage in this case however is that the choice of the best direction of projection and the setting of the C-arm position and the multi-stage optimization which may be required are undertaken during fluoroscopy so that the patient is subjected to a certain dose of radiation even before the actual intervention.

SUMMARY OF THE INVENTION

The problem underlying the invention is thus that of specifying a method of the type mentioned at the start in which the radiation dose affecting the patient is reduced and the time required for the procedure is reduced.

To resolve this problem a method for pre-interventional planning of a 2D fluoroscopy projection for an interventional entry using a fixed instrument with the features of the claims is provided.

With the inventive method a 3D data set is first recorded. This can usefully be done using computer tomography, magnetic resonance tomography or 3D angiography. This is followed in the inventive method by the planning of the intervention. This planning can include the definition of the target area for the instrument, the definition of the path and the entry point. When the planning of the instrument channel is completed, the optimum direction of projection is planned. Depending on the complexity of the intervention and of the access, a number of optimum directions of projection can also be defined, between which a switch is made during the intervention. The significant aspect here is that the planning of the optimum direction of projection is undertaken without subjecting the patient to extra radiation. Within the context of this planning the best possible visualizations of the instrument as well as of the critical structure are determined.

Subsequently the 3D data set is registered with a navigation system and with a 2D fluoroscopy system. The navigation system can for example be a stereotactic frame which allows a precise application of the instrument. In the next step the data of the planned direction of projection is transmitted to the navigation system. On the basis of this intervention data the required position of the fluoroscopy system is calculated. This definition of the position of the fluoroscopy system is undertaken automatically on the basis of the intervention data, accordingly the step-by-step adjustment for the optimum position for the fluoroscopy usual in the prior art is not necessary.

If both the navigation system and also the fluoroscopy system are correctly set, the intervention with the Instrument under fluoroscopy in the previously planned angulation can be started. With the inventive method there can be provision for the fluoroscopy system to feature a C-arm of which the position is calculated and set automatically.

To visualize critical structures such as vessels, organs and vertebrae, the projection of the 3D data set can be presented overlaid with the 2D fluoroscopy image. This is especially useful if the investigation area has low contrast. In these cases a manual optimization of the projection under fluoroscopy can only be achieved with great difficulty.

With the inventive method the position of the instrument can be checked using computer tomography, magnetic resonance tomography or 3D angiography, if necessary the method can be continued with the planning of the intervention. Thus the optimum direction of projection and setting of the position of the fluoroscopy system is planned once again.

The inventive method is especially suitable for fixed instruments such as a biopsy needle, an aspiration needle or an ablation device.

BRIEF DESCRIPTION OF THE DRAWINGS

Further advantages and details of the invention will be explained on the basis of an exemplary embodiment which refers to the figures. The figures are schematic diagrams and show.

DETAILED DESCRIPTION OF THE INVENTION

Figure 1:
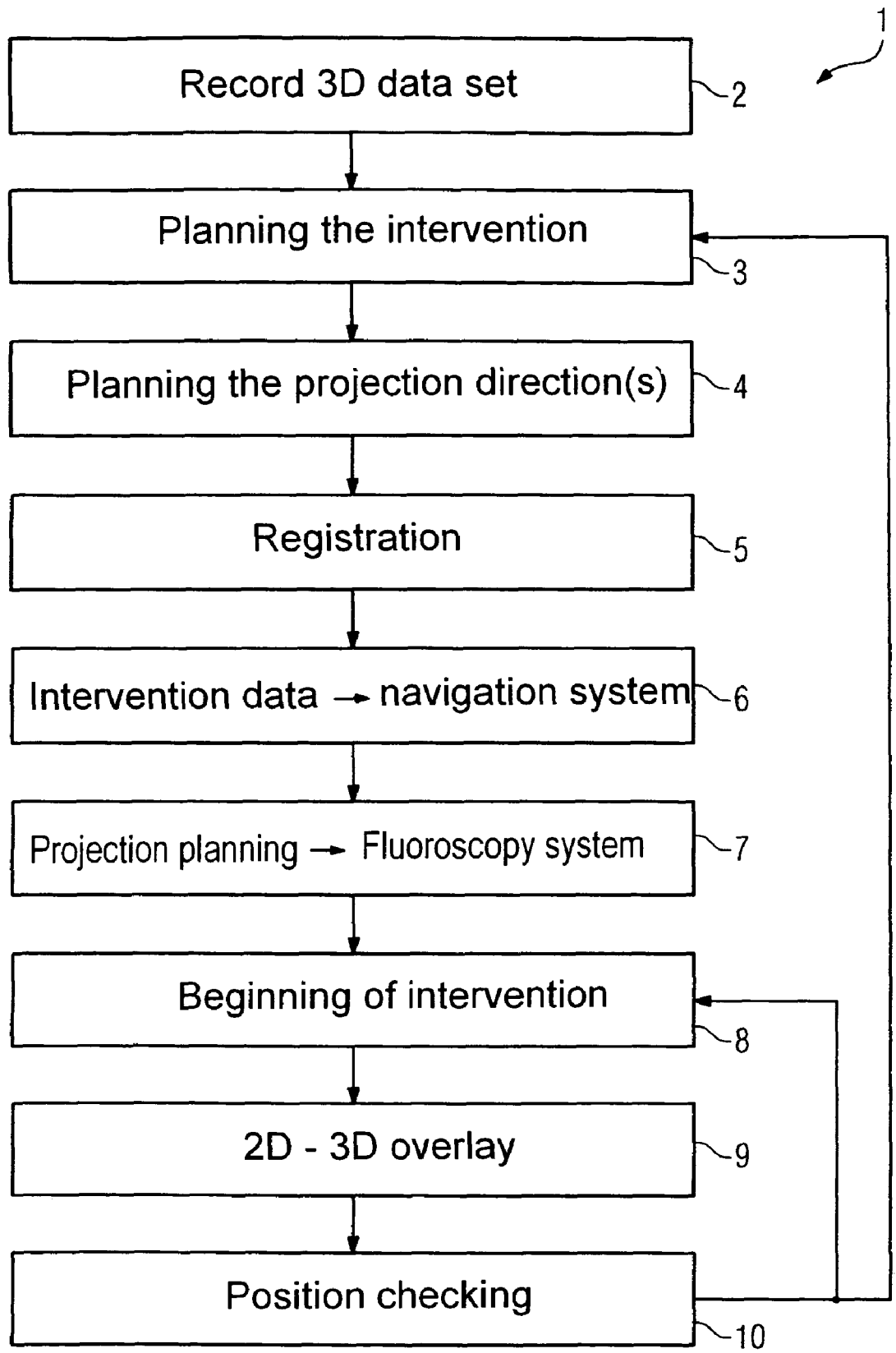
FIG. 1 a flowchart with the most important steps of the method in accordance with the invention.

The method 1 shown in FIG. 1 in the form of a schematic flowchart for pre-interventional planning of a 2D fluoroscopy projection for an interventional entry using a fixed instrument comprises the following steps: Before the intervention a 3D data set is recorded in step 2 using a method such as 3D angiography, computer tomography or magnetic resonance tomography. Subsequently the intervention is planned 3, in particular the projection directions of the instrument, for example an aspiration needle, are planned 4.

Figure 2:
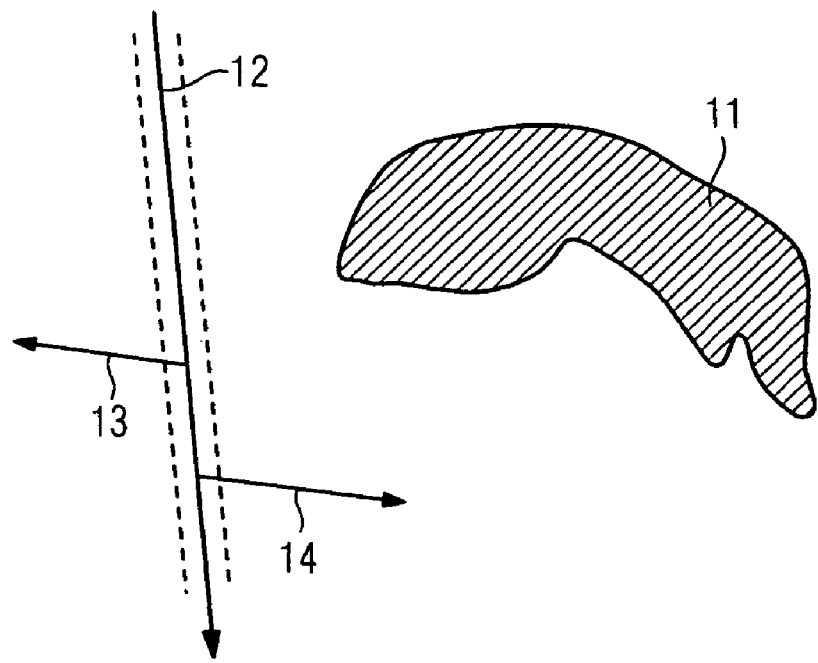
FIG. 2 a planned needle channel running alongside a critical structure.

Reference is made simultaneously to FIG. 2.

FIG. 2 shows a planned needle channel running alongside a critical structure.

A critical structure 11, in the exemplary embodiment depicted, an organ of a patient, is located in the vicinity of a needle channel 12 indicated by an arrow. The structure 11 and the needle channel 12 are objects in a three-dimensional space. The task within the context of pre-interventional planning consists of finding an optimum direction of projection for the fluoroscopy. This direction or the associated plane which lies perpendicular to the direction of projection, is defined by the best visualization of the critical structure 11 in relation to the needle channel 12 and allows an especially secure monitoring of the needle movement during the intervention.

The optimum direction of projection is defined and planned interactively by the user. The optimum direction of projection is a straight line which is perpendicular to the needle channel 12. FIG. 2 shows two typical projection directions 13, 14. The user can move away from these projection directions which are determined from the recorded 3D data and visualized on a screen, and selects an optimum visualization. Projections which cannot be set on the C-arm of the fluoroscopy device or projections at an extreme angle are not presented or a warning is displayed. In this case the user can manually deviate from the optimum values.

Again referring to FIG. 1, in the next step a registration 5 of the 2D fluoroscopy system with 3D data set is performed in order to match the coordinate systems to each other. Provided the patient is located in the same spatial position as during the intervention when the 3D data set is recorded, the registration can be dispensed with if necessary. In this case the coordinate systems coincide at least approximately.

If the 3D data set has been recorded on the same C-arm by means of 3D rotation angiography, the required registration of the patient with the 3D data set and the fluoroscopy system is automatically provided by the device calibration.

Where 3D data from other sources such as magnetic resonance tomography or computer tomography is used, automatic or interactive image registration methods can be used. It is also possible, to initially register an external data set with 3D/3D registration with the 3D rotation angiography data set, in order to implicitly establish the registration with the fluoroscopy system in this way.

In the next step shown in FIG. 1 the defined intervention data 6 is transmitted to a navigation system. In this exemplary embodiment the navigation system is a stereotactic frame. Subsequently the data determined within the context of the projection planning 7 previously undertaken is transmitted to the fluoroscopy system. This enables the required position of the C-arm to be determined, so that the critical structure 11 and the needle can be seen on the fluoroscopy image in the optimum direction of projection. This position can be reached manually by restricting the movement options of the C-arm which are entered via the user Interface. Through this restriction the C-arm can only to be moved up to the optimum position direction and is then stopped. The fact that the optimum position has been reached is indicated by an optical or audible signal. The unit can however also be moved to the optimum position automatically. This automation is only intended to assist the user in reaching the optimum position, but it is however possible at any time to depart from the predetermined settings and move the C-arm as required.

Figure 3:
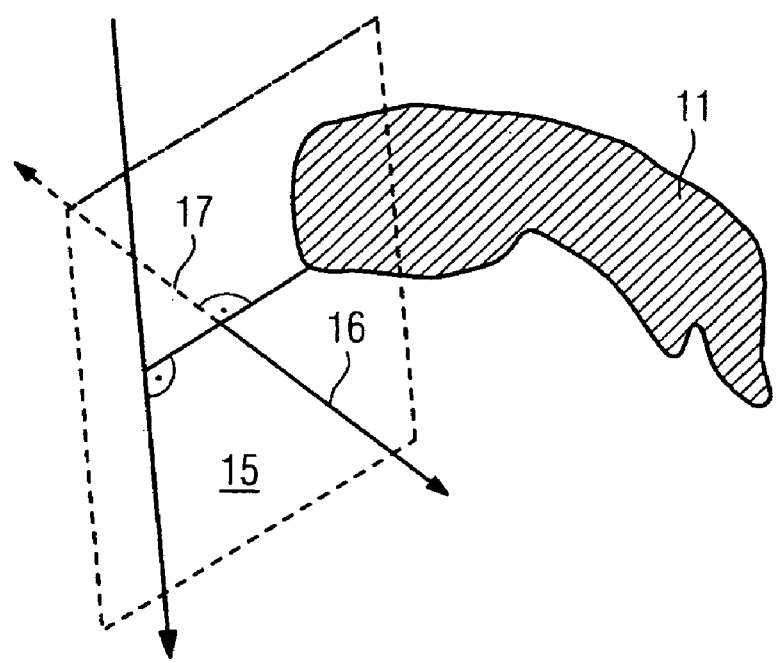
FIG. 3 the diagram shown in FIG. 2 with the optimum projection directions indicated.

If the optimum direction of projection is to be determined automatically, the normal to the surface must be determined on a plane which is produced by the needle channel 12 and the point on the critical structure closest to the needle 11. This plane 15 is shown in FIG. 3. At right angles to this plane 15 are two projection directions 16, 17, which are aligned opposite to each other and which both produce an optimum presentation. Since the projection directions 16, 17 are normals on the plane 15 they can be obtained by defining the plane 15 by the shortest connection between the critical structure 11 and the needle channel 12. As shown in FIG. 3, two possible projection directions 16, 17 are produced of which one is selected manually or automatically. If a technically impossible or critical angulation is present, a warning is displayed at the user interface.

Optionally the selection of the optimum projection direction can be undertaken on the basis of minimum x-ray absorption. The x-ray absorption is determined from the 3D angiography, the CT or the MR investigation and the corresponding 3D data set. This criterion in particular excludes projections at extreme angles or unfavorable projections because of bone structures or at least identifies them as such, so that the user can change the planning.

If a structure with low contrast is involved, as is shown in FIG. 1, after the beginning of the intervention 8 an overlaying 9 of the projection from the 3D recording onto the 2D fluoroscopy image can be undertaken.

Figure 4:
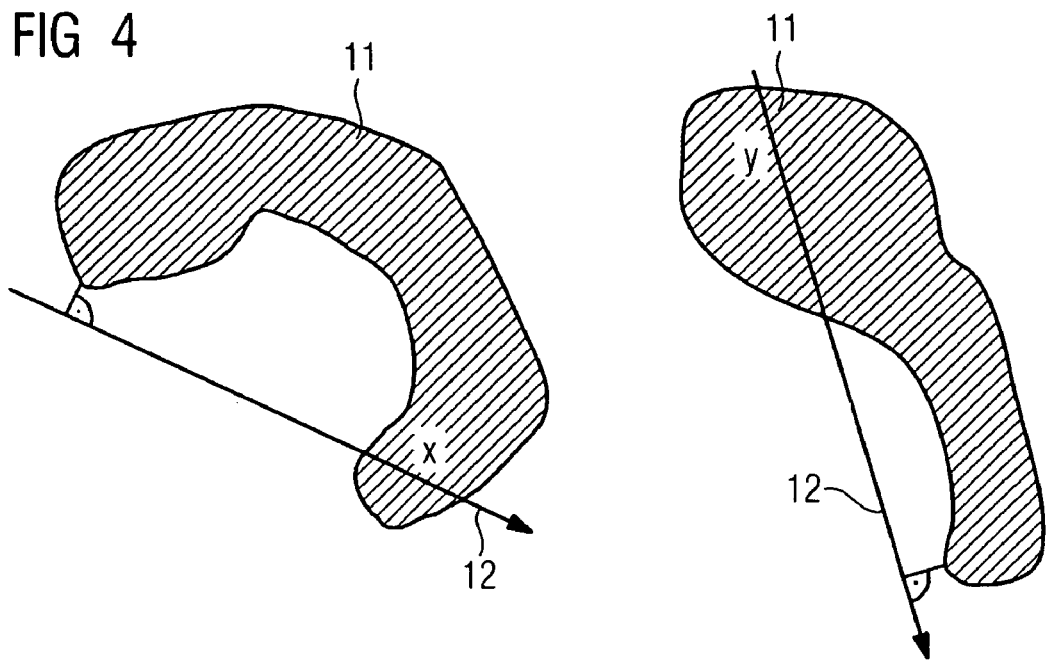
FIG. 4 two projections of a critical structure.

FIG. 4 shows two projections of a critical structure.

The critical structures can be determined automatically. After a critical distance to the needle channel 12 has been specified, with the distance amounting to 5 mm for example, the structures are determined automatically by a computer for which this critical distance is undershot and these are displayed to the user. The user can then decide for himself whether the structure is critical or not. Before the beginning of the intervention the user can create a first fluoroscopy image to ensure that the critical structure with the virtually displayed planned needle channel and where necessary the target structure for the needle can be seen as well as possible. If equally valid needle channels are present, the planning of the intervention can be optimized in order to define the optimum direction of projection or the optimum directions of projection. Following a position check 10 an update of the planning and thereby of the optimum direction of projection can be undertaken. In the flowchart shown in FIG. 1 this process is represented by the branch from the position check 10 back to the planning 3 of the intervention. The optimized direction of projection is passed on to the fluoroscopy system, the C-arm is moved accordingly and the intervention can be continued.

The optimum projection can change during the course of the intervention at different penetration depths of the needle and with different critical structures which are passed. The critical points in the two projections are indicated in this case by "x" or "y". Referring to the diagram shown in FIG. 4, it can be seen that with specific structure geometries, two or more projection directions are necessary. In advance of the intervention the relevant direction of projection can be correlated with the depth of penetration of the needle. This is shown schematically in FIG. 5 which shows the needle depth on the horizontal axis and the angulation of the C-arm of the fluoroscopy device on the vertical axis. The information about the depth of penetration of the needle from the navigation system is used, to refer the user to the depth-dependent optimum projection plane, so that this optimum projection plane can be adapted automatically or semi-automatically. This can be done interactively on the C-arm, with the C-arm only rotating around the needle channel and the rest being blocked. The left-hand section of FIG. 5 corresponds to the left-hand projection shown in FIG. 4. The angle of angulation initially remains constant as the needle depth increases, until a limit value is reached and a switch is made to another angle of angulation, which is assigned to the projection shown on the right in FIG. 4.

The needle tip position defined, measured or calculated by the navigation system can be used to update the optimum direction of projection. Alternatively the current needle tip position can be determined manually, by clicking on it with the mouse for example, or through automatic detection from images which have been recorded in two different directions of projection.

Taking into account critical structures and where necessary further criteria, varying optimum projection directions are produced along the needle channel depending on the current needle tip position. In an extreme case the direction can be changing constantly during navigation through a network of vessels, but this is time-consuming and inconvenient. In this case an attempt is made to keep the change of the angulation of the C-arm as small as possible during the advance, this value can for example be quantified as an overall angle covered. Simultaneously during the advance a specific degree of sub-optimality of the projections can be allowed, with such a value for example being able to be set as ±20°.

Figure 5:
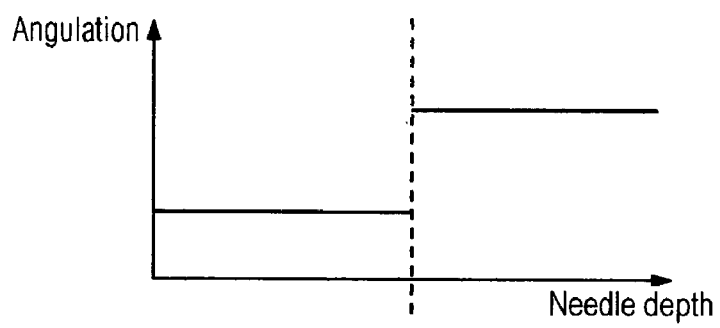
FIG. 5 a graphical presentation of the angulation and the associated needle depth of the projections of FIG. 4.
Figure 6:
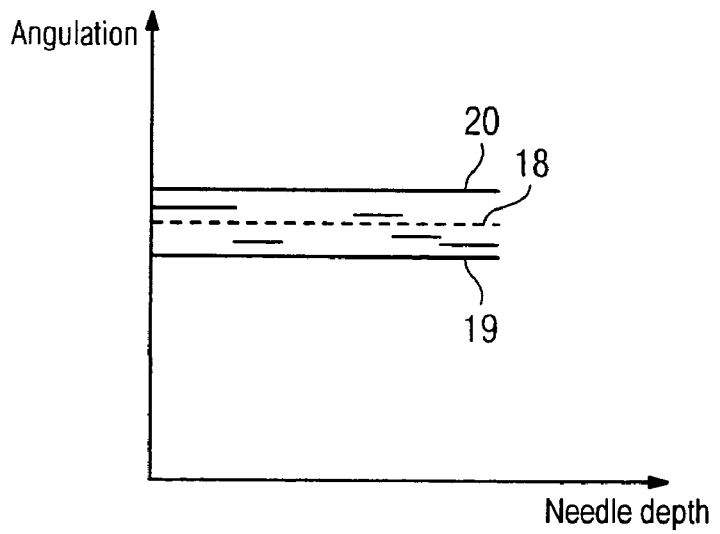
FIG. 6 a graphical presentation of the angulation and the needle depth with the tolerance range indicated.

FIG. 6, in a similar way to FIG. 5, shows a graphical presentation of the angulation over the needle depth. The dashed line specifies the averaged angulation 18 which is surrounded by a tolerance range with a lower and an upper limit value 19, 20. An iterative optimization algorithm then finds the optimum path, with the criteria "overall change of angle" and "optimality of the projection" being able to be weighted separately. In this way a compromise between perfect angulation and frequent angulation changes can be achieved. This restriction in the changes of angulation makes operation easier for the user, since few spatial reorientations are required, in addition there is a saving in contrast media for vessels and the movement time of the C-arm is reduced.

The invention claimed is:

1. A method for pre-interventional planning a 2D fluoroscopy projection of an intervention into a patient using an instrument, comprising:
    recording a 3D data set of the patient prior to the intervention;
    planning the intervention;
    defining an optimum projection direction of the intervention;
    registering the 3D data set with a 2D fluoroscopy system having a navigation system;
    transmitting the optimum projection direction to the navigation system;
    computing a position of a C-arm of the 2D fluoroscopy system; and
    executing the intervention monitored under the 2D fluoroscopy system.

2. The method as claimed in claim 1, wherein the 3D data set is recorded using a method selected from the group consisting of: computer tomography, magnetic resonance tomography, and 3D angiography.

3. The method as claimed in claim 1, wherein the step of planning the intervention defines a target area, a path and an entry point for the instrument.

4. The method as claimed in claim 1, wherein the navigation system is selected from the group consisting of: a stereotactic frame, a magnetic navigation system, and an optical navigation system.

5. The method as claimed in claim 1, wherein the 2D fluoroscopy system is a C-arm fluoroscopy system.

6. The method as claimed in claim 1, wherein the position of the C-arm is set automatically.

7. The method as claimed in claim 1, wherein a projection from the 3D data set is overlaid with a 2D fluoroscopy image recoded by the 2D fluoroscopy system.

8. The method as claimed in claim 1, wherein a position of the fixed instrument is checked during the intervention.

9. The method as claimed in claim 8, wherein the checking uses a method selected from the group consisting of: computer tomography, magnetic resonance, and 3D angiography.

10. The method as claimed in claim 8, wherein steps of the planning, defining, registering, transmitting, computing, and executing are repeated based on the checked position of the fixed instrument.

11. The method as claimed in claim 1, wherein the instrument is fixed and selected from the group consisting of: a biopsy needle, an aspiration needle, and an ablation device.

12. The method as claimed in claim 1, wherein a plurality of optimum projection directions of the intervention are defined and a switch between the optimum projection directions occurs during the intervention.

13. The method as claimed in claim 1, wherein the registering step is deleted if the patient is placed in a position identical to the position in which the patient was placed when the 3D data set was recorded.

* * * * *